United States Patent [19]

Drake

[11] 4,283,227
[45] Aug. 11, 1981

[54] ZNO—SEO$_2$—R$_2$O SOLUBLE GLASS

[75] Inventor: Cyril F. Drake, Harlow, England

[73] Assignee: International Standard Electric Corporation, New York, N.Y.

[21] Appl. No.: 75,617

[22] Filed: Sep. 14, 1979

[30] Foreign Application Priority Data

Sep. 26, 1978 [GB] United Kingdom ............... 38222/78

[51] Int. Cl.$^3$ .................. C03C 3/12; A61K 33/04
[52] U.S. Cl. .................. 106/47 R; 65/134; 424/162; 424/127
[58] Field of Search ............... 106/47 R, 52

[56] References Cited

U.S. PATENT DOCUMENTS 2,979,865   4/1961   Rough ............................ 106/52
4,123,248  10/1978   Drake ............................ 71/4

FOREIGN PATENT DOCUMENTS 16018   of 1893   United Kingdom .............. 106/47 R
1512637  6/1978   United Kingdom .

OTHER PUBLICATIONS

Chem. Abstr. 74 (1971) item 146916c "Reacton of Selenium Dioxide with Zinc Oxide in Salt Melts".
Rawson, H.-"A Note on Glass Formation in the System K$_2$O—SeO$_2$"-Physics & Chemistry of Glasses, vol. 1, No. 5 Oct. 1960, p. 170.
Weyl, W. A.-*Coloured Glasses*-pub. by Soc. of Glass Technology, Sheffield, Eng. (1951, 1967) pp. 288-291.
Rawson, H.-*Inorganic Glass-Forming Systems*-pub. by Academic Press, NYC (1967) p. 212.

*Primary Examiner*—Helen M. McCarthy
*Attorney, Agent, or Firm*—John T. O'Halloran; David M. Quinlan

[57] ABSTRACT

A subcutaneous implant for supplying one or more trace elements to an animal. The implant is made from a zinc oxide based glass which is prepared in rod form, a short section of the rod being implanted under the skin of an animal. Typically the glass may contain selenium dioxide for supplying small quantities of selenium to the animal.

6 Claims, No Drawings

ZNO—SEO₂—R₂O SOLUBLE GLASS

BACKGROUND OF THE INVENTION

1. Field of the Invention

This invention relates to glass compositions and in particular to water soluble glasses for the supply of trace elements into the bloodstream of animals by means of a subcutaneous implant.

2. Description of the Prior Art

One of the problems involved in the husbandry of domesticated animals, e.g. cattle and sheep, is the provision of an adequate supply of trace elements. For example it has been found that, for the healthy growth of such animals, it is necessary that they ingest between 1 and 5 parts per million of selenium based on body weight. In some pastures such a level of selenium occurs naturally but in other areas, e.g. in areas of high rainfall, the natural selenium level is insufficient and must therefore be supplemented either in the form of medication or as an additive to the animal foodstuff. In practice however, because the required quantities of trace elements are so small, it is difficult to achieve the required dosage rate. Furthermore, at levels above the required dose, trace elements are in general dangerous poisons.

SUMMARY OF THE INVENTION

One object of the invention is to provide a water soluble glass composition adapted to release selenium into an aqueous solution, the composition including a fused mixture of 40 to 60 mol % selenium dioxide ($SeO_2$) and 35 to 60 mol % zinc oxide (ZnO) and the balance, if any, including one or more metal or non metal oxides.

Another object of the invention is to provide a subcutaneous implant for an animal, adapted to supply one or more trace elements into the bloodstream of the animal, the implant comprising a body of a glass material at least the major portion of which includes one or more oxides of said one or more trace elements together with zinc oxide.

A further object of the invention is to employ a glass as a subcutaneous implant.

The above mentioned and other features and objectives of this invention will become more apparent by reference to the following description.

DESCRIPTION OF THE PREFERRED EMBODIMENTS

A subcutaneous implant for an animal must be non-toxic, a non-irritant and able to dissolve at a suitable rate so as to supply an adequate level of one or more trace elements into the body fluids of an animal in which the glass is implanted. We have found that glasses based on zinc oxide, which acts as a glass modifying oxide, may be used for this purpose.

The term "glass modifying oxide" is understood to mean an oxide which, while it does not of itself form a glass, is capable of forming glass compositions in conjunction with other, generally oxide, glass forming materials. In the glass compositions described herein the trace element or elements may be present in the form of glass forming oxides or as additives together with one or more biologically inert or active glass forming oxides. The components of the glass composition are fused and thoroughly mixed and the melt is then cast e.g. into a rod. A portion of such a glass rod may then be inserted beneath the skin of an animal where the glass constituents slowly dissolve into the animals bloodstream.

In particular, glass compositions suitable for supplying controlled quantities of selenium e.g. to an animal, may be prepared from selenium dioxide ($SeO_2$) and zinc oxide (ZnO) as the major constituents together with oxides of other metals or non-metals as minor constituents. These latter minor constituents may be employed to determine the water solubility, and hence the selenium release rate of the glass composition. The technique of solubility adjustment is more fully described in British Pat. No. 1,512,637. It has been found in general that the upper limit for the molecular percentage of selenium dioxide in such glass compositions is 60 mol %, above which the glass composition devitrifies. Also, at selenium concentrations below 40 mol %, the glass is hygroscopic and thus unsuitable for controlled selenium release. Small quantities of metal oxides, e.g. alkali metal oxides, may be incorporated in the glass composition to adjust the softening point, ensure freedom from devitrification, and to control the rate of solution. Thus, for example, for glasses of the molar composition $xM_2O:(50-x)ZnO:50SeO_2$ where $M_2O$ is an alkali metal oxide or a mixture of alkali metal oxides, those glasses wherein $x<5$ are effectively insoluble while those wherein $x>18$ disintegrate rapidly in water. Therefore, to obtain a useful composition, x should lie within the range 5 to 18.

The glass is prepared by mixing the constituent oxides, i.e. zinc oxide, selenium oxide and optionally other metal and/or non-metal oxides, in dry powder form. The mixture is fused into a homogeneous material at a temperature of 500° to 700° C. for 10 min. to 1 hr. in an air atmosphere. Conveniently the glass may be fused in a platinum crucible. The melt may then be cast and cooled. Advantageously the glass composition is formed as a small smooth body, e.g. by drawing into a rod which is then subdivided into short lengths, which may be implanted beneath the skin of an animal so as to release selenium directly into the animal's body fluids.

It will be clear to those skilled in the art that the carbonate, hydroxide nitrate etc. of one or more constituent metals may be used in place of the metal oxide as those components decompose to form the respective oxide during the fusion process.

The following examples illustrate the invention:

EXAMPLE 1

0.67 g anhydrous sodium carbonate, 1.28 g potassium nitrate, 5.6 g selenium dioxide and 4.0 g basic zinc carbonate were fused for 15 mins. in a platinum crucible at a temperature of 600° C. and in an air atmosphere. The total weight loss on fusion was 2.38 g, this loss being attributed to the evolution of $CO_2$, $NO_2$, $O_2$, $H_2O$ and some $SeO_2$. The final composition of the clear yellow glass was:

$Na_2O$—6.59 mol % 4.3 wgt. %
$K_2O$—6.61 mol % 6.5 wgt. %
ZnO—36.61 mol % 31.1 wgt. %
$SeO_2$—50.19 mol % 58.1 wgt. %

A 3 mm rod drawn from this melt was immersed in new-born calf serum at a temperature of 38° C. and was found to dissolve at a rate of 0.53 mg/day.

EXAMPLE 2

A glass composition was prepared containing 50.6 mol % 57.5 wgt. % selenium dioxide; 38.6 mol % 32.1 wgt. % zinc oxide and 10.8 mol % 10.4 wgt. % potassium oxide (K$_2$O).

The glass was cast, allowed to cool and was then crushed. A weighed portion of the glass was immersed in new-born calf serum at a temperature of 38° C. The dissolution rate of the glass under these conditions was found to be 25 μg/cm$^2$/hr.

I claim:

1. A water soluble glass composition adapted to release trace amounts of selenium into an aqueous solution, the composition including a fused mixture of 40 to 60 mol % selenium dioxide (SeO$_2$) as a glass-forming oxide and 35 to 60 mol % zinc oxide (ZnO) as a glass-modifying oxide as its major constituents and at least one alkali metal oxide as a minor constituent for modifying the selenium release rate, wherein the alkali metal oxide molar concentration is at least as low as 13.1%.

2. A water soluble glass composition adapted to release trace amounts of selenium into an aqueous solution, the composition including a fused mixture of selenium dioxide (SeO$_2$) as a glass-forming oxide and zinc oxide (ZnO) as a glass-modifying oxide as its major constituents and at least one alkali metal oxide as a minor constituent for modifying the selenium release rate, wherein the molar composition of said glass composition is substantially xM$_2$O:(50−x)ZnO:50SeO$_2$, M$_2$O is the alkali metal oxide content and the value of x is between 5 and 18.

3. A water soluble glass composition as recited in claim 2, comprising 5 to 8 mol % Na$_2$O, 5 to 8 mol % K$_2$O, 35 to 38 mol % ZnO, and 49 to 51 mol % SeO$_2$.

4. A water soluble glass composition as recited in claim 3, comprising
   6.59 mol % Na$_2$O,
   6.61 mol % K$_2$O,
   36.61 mol % ZnO, and
   50.19 mol % SeO$_2$.

5. A water soluble glass composition as recited in claim 2 comprising 49 to 51 mol % SeO$_2$, 37 to 40 mol % ZnO and 9 to 12 mol % K$_2$O.

6. A water soluble glass composition as recited in claim 5, comprising
   50.6 mol % SeO$_2$,
   38.6 mol % ZnO, and
   10.8 mol % K$_2$O.

* * * * *